United States Patent
Schneider

(10) Patent No.: US 7,534,104 B2
(45) Date of Patent: May 19, 2009

(54) ADAPTER FOR LIGHT EMITTING APPARATUS USED IN THE MEDICAL FIELD

(75) Inventor: Rainer Schneider, St. Pantaleon (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 51 days.

(21) Appl. No.: 10/781,030

(22) Filed: Feb. 17, 2004

(65) Prior Publication Data
US 2004/0166464 A1    Aug. 26, 2004

(30) Foreign Application Priority Data
Feb. 20, 2003   (AT)   ................ A 253/2003

(51) Int. Cl.
*A61C 1/00* (2006.01)
(52) U.S. Cl. ............ 433/29; 439/956; 363/63; 361/245
(58) Field of Classification Search ............ 433/29; 439/21, 956; 363/63; 361/245–246
See application file for complete search history.

(56) References Cited

U.S. PATENT DOCUMENTS

| | | | | |
|---|---|---|---|---|
| 3,042,835 A | * | 7/1962 | Badger | 315/171 |
| 3,215,139 A | * | 11/1965 | Dietz | 604/20 |
| 3,626,354 A | * | 12/1971 | Banner | 439/105 |
| 4,204,243 A | * | 5/1980 | Ross | 361/245 |
| 4,720,266 A | * | 1/1988 | Leonard et al. | 433/126 |
| 4,804,329 A | * | 2/1989 | Nakayama et al. | 439/20 |
| 5,057,015 A | * | 10/1991 | Fleer | 433/126 |
| 5,593,323 A | * | 1/1997 | Dernehl | 439/668 |
| 5,653,591 A | * | 8/1997 | Loge | 433/118 |
| 5,860,975 A | * | 1/1999 | Goble et al. | 606/45 |
| 6,033,220 A | * | 3/2000 | Mosimann | 433/126 |
| 6,305,934 B1 | * | 10/2001 | Hatley, Jr. | 433/80 |
| 6,638,063 B2 | * | 10/2003 | Otsuka | 433/29 |

FOREIGN PATENT DOCUMENTS

| EP | 1103232 A1 | * | 5/2001 |
|---|---|---|---|
| FR | 2 818 892 | | 12/2000 |

* cited by examiner

*Primary Examiner*—Ralph A Lewis
(74) *Attorney, Agent, or Firm*—Klarquist Sparkman, LLP

(57) ABSTRACT

An adapter for a handpiece system, especially for use in conjunction with medical and dental light emitting apparatus for the transmission of light to cure photo-polymerisable materials. A device, preferably in the form of an adapter, enables the user to correctly match the polarity of the contacts in the supply hose or conduit with those of the light emitting apparatus.

27 Claims, 3 Drawing Sheets

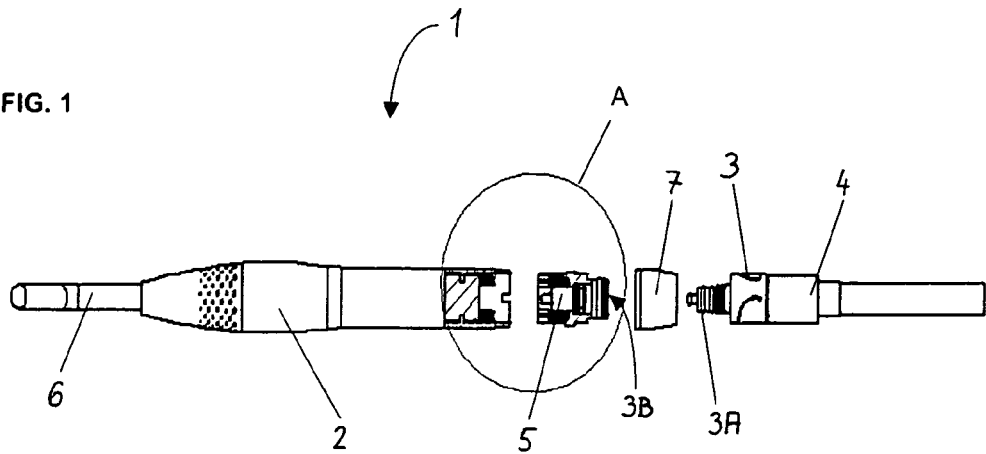
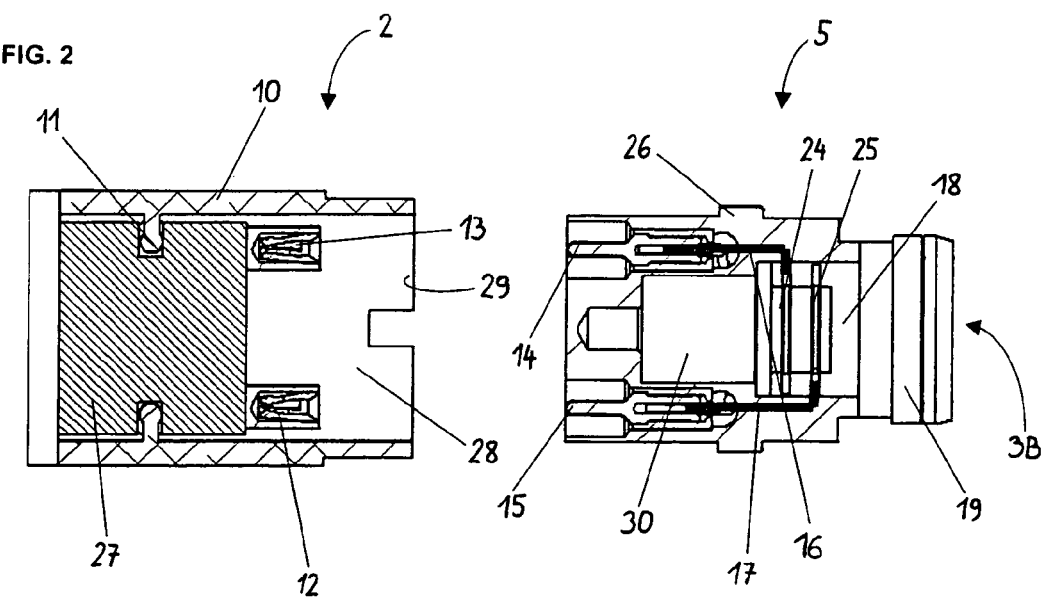
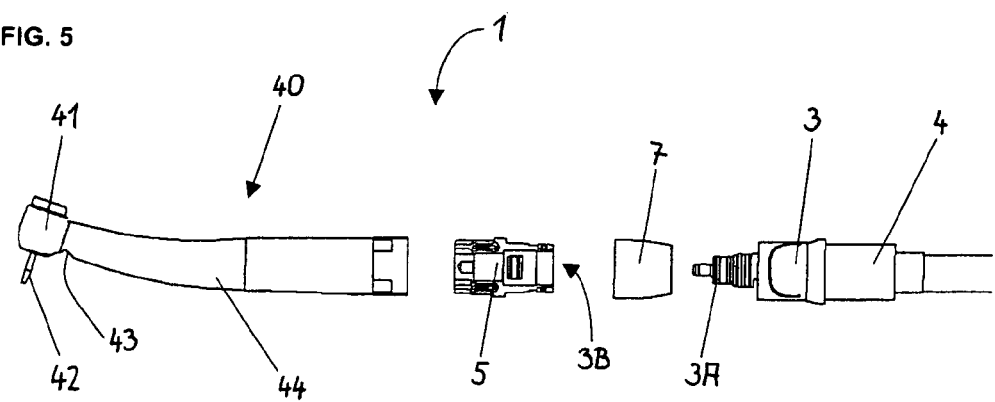

ADAPTER FOR LIGHT EMITTING APPARATUS USED IN THE MEDICAL FIELD

CROSS REFERENCE TO RELATED APPLICATION

The present application claims priority from pending Austrian Patent Application No. A 253/2003, filed Feb. 20, 2003, which is incorporated herein by reference.

BACKGROUND OF THE INVENTION

1. Field

The invention presented here concerns an adapter for a handpiece system, especially for use in conjunction with medical and dental light emitting apparatus for the transmission of light such as may be used to cure photo-polymerisable materials, particularly for the filling of cavities and securing of braces, as well as for providing proof of caries or for bleaching the surface of teeth.

2. Description of Prior Art

The power supply for light emitting apparatus of this kind is provided either by means of batteries, which are housed in the hand-held equipment, as described in the FR 2818892 A1, for example, and/or through connection to an external power, or voltage source. As a preference, this is effected by coupling the light emitting apparatus to a supply hose, or conduit, provided for those air-driven appliances present in a dental unit. This enables the light emitting apparatus to be used as part of the existing, familiar unit without incurring any additional procurement costs for control devices.

Supply hoses for air-driven appliances contain several media supply lines, including a twin-pole power lead for a power supply with voltage of 3.3V. In accordance with certain standards, such as European Standard, EN 29168 (=ISO 9168), the two ends of the power lead exit at a prescribed point in the form of electrical contacts, located at an appropriate distance from other media supply lines and integral with the plane surface ending at the connection of the supply hose. This standard, however, contains no directions with regard to the arrangement of the two contacts' polarity and this is not noted during assembly of the dental unit or connection of the supply hoses, which in the end means that it is impossible to tell which of the two contacts represents the positive or negative poles. This is not necessary in usual practice, since small light bulbs located in the air-driven appliances for merely illuminating the preparation area are fed via these contacts, and they light up irrespective of the polarity arrangement.

In contrast to this, it is an absolute necessity to identify the polarity of the supply hose contacts when operating specialized light emitting apparatus (and before its initial use) and to match this polarity to that of the contacts of the light emitting apparatus, since light-emitting diode(s) (LED) used in the light emitting apparatus rely on correct connection.

Determining the polarity of the two contacts is a task currently carried out by a service technician, who has to make a special trip to the user for this purpose. If the polarity of the contacts of the supply hose does not match the contact arrangement in the light emitting apparatus, then the technician cross-plugs the connections of the supply hose in the dental unit.

One manufacturer provides a test appliance with each piece of light emitting apparatus, with the aid of which the user can himself establish whether the contact arrangement in the supply hose matches that in the light emitting apparatus. But even in this case a service technician has to carry out any possibly necessary correction to the supply hose connection. Both variants, therefore, are extremely time consuming and costly.

Because of this, there exists an urgent need for a simpler and cheaper solution which enables the user himself to put the light emitting apparatus into operation without specialist support.

SUMMARY OF THE INVENTION

This task is, in accordance with the invention presented here, resolved by a device, e.g. in the form of an adapter which accommodates matching the polarity of contacts within a handpiece system including at least two separable components.

Another aspect of the invention is to provide light-emitting apparatus for a handpiece system with a light source contained therein and contacts for connecting to an external power source, and an adapter to match the polarity of contacts.

In accordance with an aspect of the invention, the adapter contains leads for providing an electrical power, or voltage supply to the light emitting apparatus, whereby these leads are either in the form of continuous, uninterrupted leads and the adapter can be rotated about its longitudinal or lateral axis in relation to the light source contacts, or the leads are subdivided into sections, comprised of rigid and movable sections, and in which different lead routings can be produced by connecting the movable sections to the rigid sections.

In one embodiment the adapter contains two leads, which in each case end adjacent both ends of the adapter in pairs as contacts, whereby the two leads are routed in such a way that they cross each other within the adapter, so that the arrangement of the contacts at both ends of the adapter is exactly reversed. The user can now insert this adapter into the handpiece system (consisting of at least one piece of light emitting apparatus and one supply hose) in any arbitrarily selected position, plug the handpiece system and adapter together and then put the system into operation and, if it is not possible to operate the light emitting apparatus, disconnect the handpiece system, turn the adapter through 180° about its lateral axis and then reconnect it to the handpiece system in this position in order to be able to subsequently operate the light emitting apparatus.

In another embodiment, the connection of the light emitting apparatus to the supply hose is made via a rotary coupling equipped with slip rings for voltage transmission at its distal end. The adapter is positioned between the light emitting appliance and the coupling, and the connection of the light source to an external voltage source is effected via slide contacts in the adapter, which make contact with the coupling's slip rings. A suitable contact is made by rotating the coupling about its longitudinal axis in relation to the contacts of the light source.

In yet another embodiment, the adapter forms part of the light emitting apparatus or of the sleeve of the handpiece system, consisting of at least one supply hose with a distal coupling device with contacts for voltage transmission from an external voltage source and one handle containing a light source, contacts for connecting the light source to an external voltage source and one proximal coupling device. This reduces the number of interfaces and break points at which dirt particles or disease pathogens can collect.

Another aspect of the invention is to provide a simplified process which enables the user, with the aid of an adapter made in accordance with the invention, to make a suitable contact without requiring the support of a service technician.

The invention is explained by means of preferred embodiments and in reference to the enclosed drawings:

BRIEF DESCRIPTION OF THE DRAWINGS

FIG. 1 shows, in the form of an exploded view, a handpiece system complete with an adapter according to an embodiment of the invention;

FIG. 2 is an enlarged longitudinal section view of the excerpt labeled A in FIG. 1.

FIG. 5 shows in exploded view a handpiece system with a handpiece turbine and an adapter.

DETAILED DESCRIPTION OF THE PREFERRED EMBODIMENTS

Figure 3A:
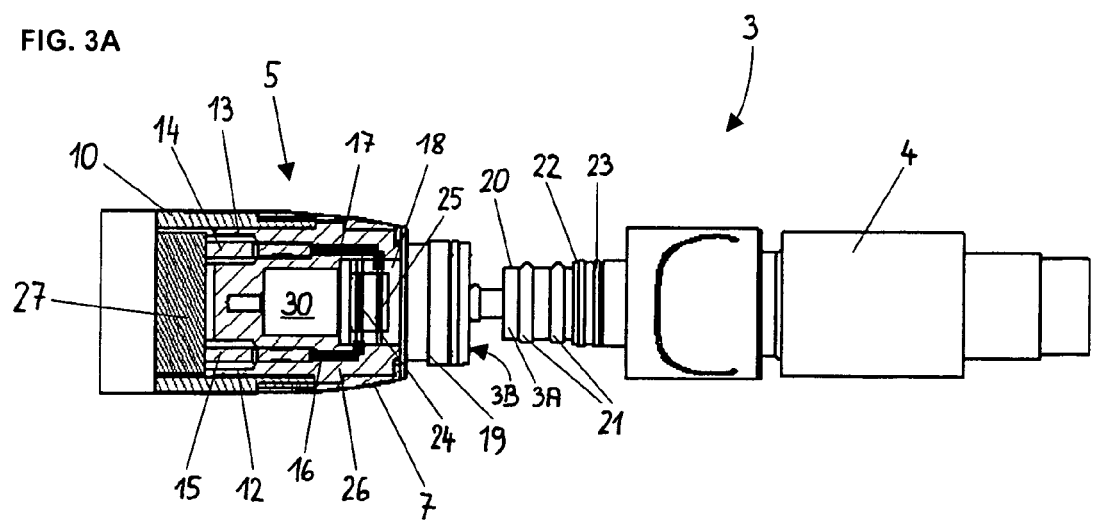
FIGS. 3A and 3B show in detail an adapter fixed into the handle sleeve at two different, predetermined positions, forming a detachable connection with the light source contacts.

The same components are labeled with the same numerals in all figures.

The descriptive terms used here, 'distal' and 'proximal', refer to orientation of the apparatus relative to the dental unit (treatment chair) to which the handpiece system is connected: "Proximal" means the side of a component nearer in the line of connection to the dental unit, whilst "distal" means the side away and further in the line of connection from the dental unit.

FIG. 1 illustrates a handpiece system I consisting of light emitting apparatus 2, a rotary coupling 3 and supply hose, or conduit, 4 in which an adapter 5, produced in accordance with the invention, is inserted. At the distal end of the light emitting apparatus 2, a light conductor 6 is arranged which conducts the light produced by a light source (not shown), also referred to as an electrical operating element, contained in the light emitting apparatus 2 to the point of treatment. The adapter 5 is designed as a component of the light emitting apparatus 2 and is fixed to the handle sleeve 10 via an end cap 7. A rotary coupling 3 is then connected, via which a connection with the supply hose 4 and an external electrical power, or voltage, source is made and which simultaneously guarantees that the light emitting apparatus 2 is free to rotate with respect to the supply hose 4.

Figure 3B:
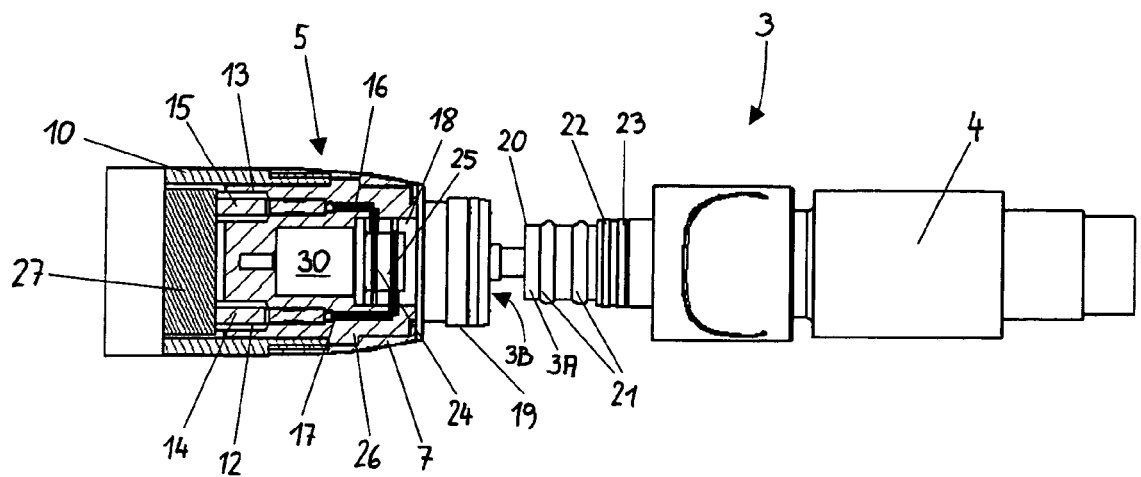

The detailed section shown in FIG. 2 corresponds to the excerpt labeled "A" in FIG. 1. Both the adapter 5 and the proximal end of the light emitting apparatus 2 can be seen. The adapter 5 consists of an adapter housing 26, through which two continuous, uninterrupted leads 16 and 17 are routed, which end at their distal points (at the left in FIG. 2) in the form of non-rotatable, detachable contacts, preferably as plug contacts 14 and 15, but whereby other types of detachable contacts, e.g. spring contacts, are conceivable. Contacts 14 and 15 of the leads 16, 17 of the adapter 5 can be plugged into plug terminals, or contacts, 12 and 13 in handle sleeve 10 by pushing the adapter 5 through the aperture 29 of the light emitting apparatus 2 into a hollow space 28 formed by the handle sleeve 10. Contact can be made through two possible, predetermined positions of adapter 5: contact 14 and plug terminal 13, as well as contact 15 and plug terminal 12, can be connected to each other (position 1) as shown in FIG. 2 and 3A. Contact 14 and plug terminal 12, as well as contact 15 and plug terminal 13, can be connected to each other by turning adapter 5 through 180° about its longitudinal axis (position 2) as seen in FIG. 3B. The voltage supply, or electrical power supply, is transmitted to circuit board 27, which is fixed to the handle sleeve 10 by means of positioning pins 11, and to the light source via plug terminals 12 and 13.

The proximal ends of leads 16 and 17 of the adapter 5 (adjacent the right end in FIG. 2) are in the form of slide contacts 24 and 25, or connectors, and project, supported by a bracket 18, radially inward. An end portion 3A of the coupling 3, connected to the supply hose 4, is inserted into the hollow space 30 of the adapter 5 via the lock 19, thus creating a handpiece system 1 which corresponds to FIG. 1. Arrow 3B in the figures points to an open end of lock 19 through which end portion 3A may be inserted.

FIG. 3A shows the adapter 5 inserted into the end piece of the handle sleeve 10, whereby plug contact 13 is connected to contact 14 and plug terminal 12 to contact 15 (corresponds to position 1). The coupling 3, which connects to the adapter 5, has a coupling spigot 20, on which two gasket rings 21 and two slip rings 22 and 23 are located. Coupling 3 is illustrated in position to be inserted axially (moving to the left in FIGS. 3A, 3B) into coupled engagement with adapter 5, such that end portion 3A enters space 30. Inserting the coupling spigot 20 into the adapter 5 produces contact between slide contacts, or connectors, 24, 25 and slip rings 22, 23. The slip rings 22 and 23 are connected to electrical leads in the supply hose 4 via leads and plug contacts in coupling 3, which means that, if the individual appliances are joined together in accordance with FIG. 1, a supply electrical power, or voltage, to the electrical operating element, or light source in the handle sleeve 10 of the light emitting apparatus is effected in the familiar manner by an external electrical power, or voltage source via contacts 12-15, leads 16, 17, their contacts 24, 25, slip rings 22, 23, coupling 3 and supply hose 4.

What may remain unknown, however, is the polarity of the two slide contacts 22 and 23, since power is normally supplied via these contacts to small light bulbs contained in air-driven appliances in order merely to illuminate the preparation area, and they light up irrespective of the polarity arrangement. In contrast to this, the LEDs used in the specialized light emitting apparatus 2 rely on the correct polarity contact arrangement being produced. This means that the contact arrangement represented in FIG. 3A might make operation of the light emitting apparatus 2 impossible, since slip ring 23, which represents the negative pole, is connected via slide contact 25, lead 17 and plug contact 14 to plug terminal 13, which, however, is connected to the positive pole of the light source. The same applies to slip ring 22 as a positive pole connected via slide contact 24, lead 16 and plug contact 15 to terminal 12, and thus to the negative pole of the light source (position 1).

However, with the aid of adapter 5, produced in accordance with an embodiment of the invention, the user can alter the contact arrangement (position 2), see FIG. 3B. To do this coupling 3 is disconnected from the adapter 5 and the adapter 5 is taken out of the handle sleeve 10, turned through 180° about its longitudinal axis into a second possible, predetermined position and then once again reinserted into the handle sleeve. The new contact arrangement now runs from slip ring 23, which represents the negative pole, via slide contact 25, lead 17 and plug contact 14 to plug terminal 12, which is connected to the negative pole of the light source, and via slip ring 22 as the positive pole, slide contact 24, lead 16 and plug contact 15 to terminal 13 and thus to the positive pole of the light source (position 2). The correct contact arrangement is thus established correctly and the light emitting apparatus can be operated. Since the adapter 5 is connected to the light source via plug contacts 12-15 in a fixed manner, and is further secured by the end cap 7 (FIG. 1), selection of the correct position by the user only has to be carried out once, as part of the initial start-up procedure for the light emitting apparatus 2.

Figure 4A:
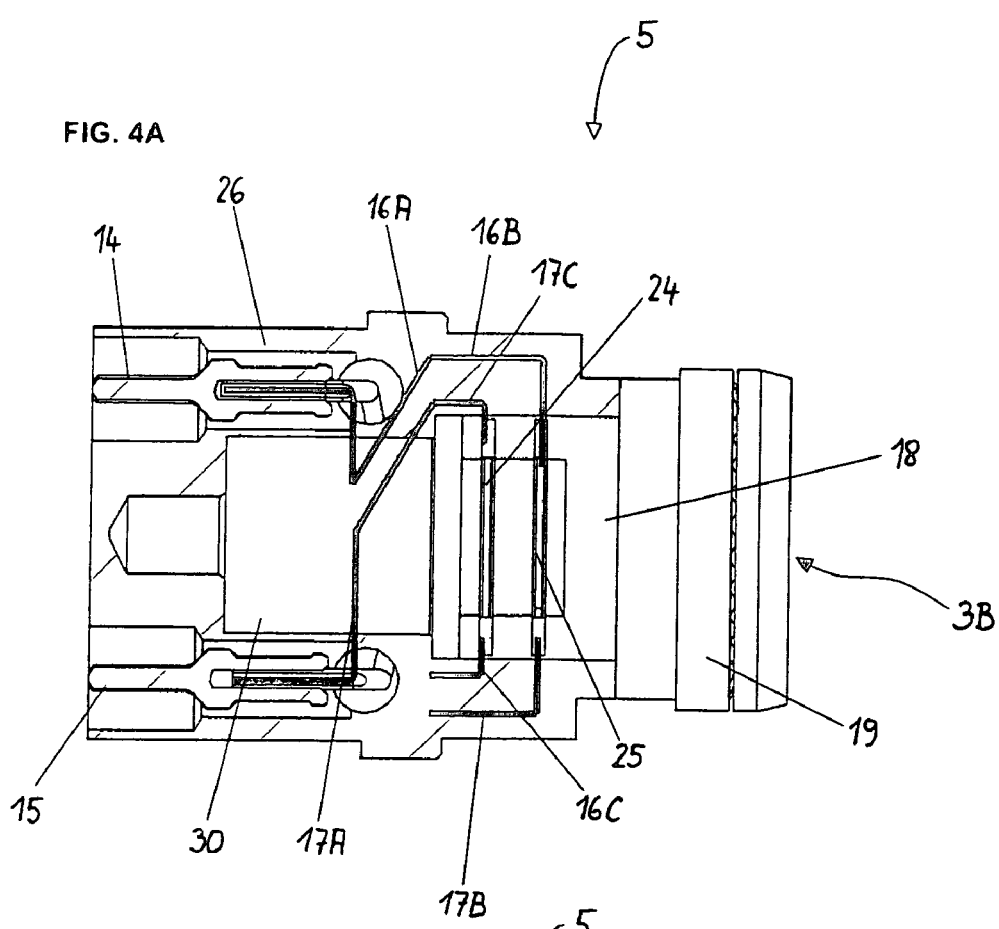
FIGS. 4A and 4B show an alternative design example of the adapter with two different modes of contact.
Figure 4B:
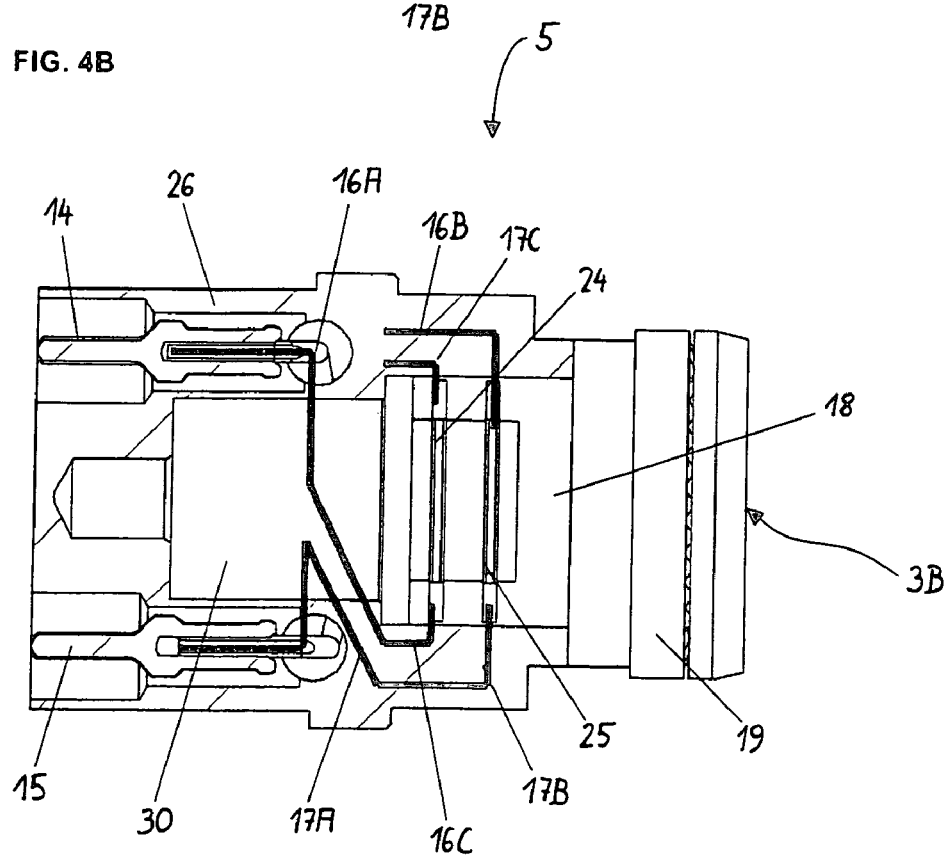

In an alternative embodiment of the adapter 5 represented in FIGS. 4A and 4B, leads 16 and 17 are divided into several sections 16A, 16B, 16C and 17A, 17B, 17C respectively. The rigid sections 16B, 16C, 17B and 17C are connected to slide contacts 24 and 25, and movable sections 16A and 17A are connected to plug contacts 14 and 15. The movable lead sections 16A and 17A can be connected to the rigid sections 16B and 17C, respectively (position 1, FIG. 4A), or to sections 16C and 17B respectively (position 2, FIG. 4B) via an operating element, in order to produce different lead routings and thus the correct contact arrangement. One advantage of this design example is simpler operation, since the user only has to undo the end cap 7 from the handle sleeve 10, without having to take the adapter 5 out of the handle sleeve 10 or the light emitting apparatus 2 and to turn the adapter into a suitable position. Contacts 12-15 in this design example can be connected to each other in a fixed manner instead of being detachable. In an especially preferred design example the switch of the adapter 5 is effectively connected to a further operating element located on the outside of handle sleeve 10, which also means that the user no longer has to undo end cap 7 in order to be able to select the desired contact arrangement.

The invention is not restricted to the depicted design examples. In particular, the adapter 5 can be in the form of an independent component or form part of any arbitrary appliance belonging to the handpiece system 1. The arrangement of the adapter 5 also is not restricted to the proximal end of the light emitting apparatus 2 or the handle sleeve 10, but rather the adapter 5 can be attached to or inserted into any component belonging to handpiece system 1.

In the case of the rotary adapter shown in FIGS. 3A and 3B, the angle of rotation between the possible, predetermined positions is not restricted to a certain dimension, but depends on the arrangement of the contacts within the component to which the adapter 5 is attached.

Moreover, the arrangement of slide contacts 24, 25 and slip rings 22, 23 to certain components is only meant to serve as an example and the opposite is possible in the sense of kinematic reversal.

In addition to use in light emitting apparatus, the adapter 5 also can be deployed in handpiece systems with other surgical and medical instruments, which are equipped with LEDs, such as, for example, turbine handpieces, motor-driven straight and contra-angled handpieces, laser handpieces, syringe devices for spraying water, scalers for removing tartar, saws, medical camera handpieces, endoscopes, mirrors or cold light sources for illuminating operation areas. As an example, FIG. 5 shows an air driven turbine handpiece 40 forming part of the handpiece system 1. The turbine handpiece 40 has a head 41 to which a tool 42, e.g. a burr, is coupled detachably via a chuck. One or more LEDs are disposed inside the turbine handpiece 40, preferably in the handle sleeve 44, either close to an opening 43 from which the light is projected onto the treatment site and the tip of the tool 42, or remote from opening 43. In the latter case the light is transmitted from the LEDs to the opening 43 via a light guide, e.g. a glass or fibre glass rod.

Usually there is also delivered a spray, consisting of a mixture of a liquid and a gas (e.g. air and water), from the head 41 to the treatment site. Both the liquid and the gas are supplied through lines which are disposed in hose 4 and pass through the coupling 3 and the handpiece 40 to the head 41. Therefore also adapter 5 must be equipped with corresponding bores or lines for the liquid and the gas, those lines preferably passing the adapter 5 on its inside.

The adapter 5 may also have bores or lines for the transmission of energy which drives tool 42, for example compressed air for a turbine handpiece. If the adapter 5 is attached to a handpiece which is driven by a motor, and the motion produced by the motor is transferred to tool 42 via a shaft, the adapter 5 may also be provided with a bore for the shaft.

What is claimed is:

1. An adapter for use in a handpiece system that includes a supply conduit and a medical instrument having an electrical operating element thereon, the adapter comprising:
   an adapter body having a first body end, a second body end, and a substantially straight longitudinal axis extending between the first and second body ends, wherein the first body end is adapted for attachment to one of the supply conduit and the medical instrument and the second body end is adapted for attachment to the other of the supply conduit and the medical instrument; and
   first and second adapter electrical leads connectable to a voltage or power supply, wherein, when the adapter is in place between the supply conduit and the medical instrument with the adapter electrical leads electrically connected to the supply conduit and to the medical instrument, electrical power is received by the adapter from the supply conduit and transmitted through the adapter to the operating element, and
   wherein the adapter is selectively switchable without disassembly by a manual operation to move the adapter leads relative to the supply conduit to match a polarity of the electrical power transmitted from the supply conduit to a polarity required by the operating element, wherein the first adapter electrical lead comprises a first end and the second adapter electrical lead comprises a second end, said first and second ends being axially offset along the longitudinal axis of the adapter body such that the first end is located a first distance from the first body end and the second end is located a second distance from the first body end, where the first distance is not equal to the second distance, wherein the adapter comprises a hollow space for releasable accommodation of a coupling spigot, and wherein said first and second ends are located at the periphery of said hollow space.

2. The adapter of claim 1, wherein the operating element has first and second contacts to which said first and second adapter electrical leads may be detachably connected in a first orientation with said first lead connected to said first contact and said second lead connected to said second contact, and said adapter is configured for rotation about an axis thereof to a second orientation whereby said first lead is connected to said second contact and said second lead is connected to said first contact to reverse the polarity of electrical power transmitted to the operating element.

3. The adapter of claim 2, wherein the operating element comprises a light source requiring electrical power to be supplied thereto in a selected polarity and said adapter is configured for detachment from said contacts and when detached may be rotated between at least two predetermined positions and reconnected to said contacts to permit selection of the polarity of electrical power transmitted from said supply conduit to said light source.

4. The adapter of claim 3, wherein said two predetermined positions are disposed at 180 degrees relative to each other.

5. The adapter of claim 1, wherein the first end and second end of the adapter electrical leads each comprises a slide contact.

6. The adapter of claim 2, wherein said leads and contacts are connected by non-rotatable plug contacts.

7. The adapter of claim 1, wherein the adapter body is configured to accommodate lines for the transmission of fluids or drive energy extending through the adapter body.

8. The adapter of claim 1, wherein the adapter is selectively switchable when connected by rotating at least a portion of the adapter body relative to the supply conduit and to the medical instrument.

9. A light emitting apparatus including a light source requiring a selected polarity of power supply connected to a supply conduit through which electrical power is transmitted and an adapter connected between the light source and the supply conduit, said adapter having an adapter body with a first body end, a second body end, and a substantially straight longitudinal axis extending between the first and second body ends, wherein the first body end is adapted for attachment to one of the supply conduit and the light source and the second body end is adapted for attachment to the other of the supply conduit and the light source, the adapter body comprising
first and second electrical leads connectible to the power supply, and being selectively switchable without disassembly by a manual operation to move the electrical leads of the adapter relative to the supply conduit to match the polarity of electrical power transmitted from the supply conduit to the selected polarity required by the light source,
wherein the first electrical lead comprises a first end and the second electrical lead comprises a second end, said first and second ends being axially offset along the longitudinal axis of the adapter body such that the first end is located a first distance from the first body end, and the second end is located a second distance from the first body end where the first distance is not equal to the second distance,
wherein the adapter comprises a hollow space for releasable accommodation of a coupling spigot, and
wherein said first and second ends are located at the periphery of said hollow space.

10. The apparatus of claim 9 wherein the light source is connected to first and second contacts to which said first and second leads may be detachably connected in a first orientation with said first lead connected to said first contact and said second lead connected to said second contact, and said adapter is configured for rotation about an axis thereof whereby said first lead is connected to said second contact and said second lead is connected to said first contact to reverse the polarity of electrical power transmitted to the operating element.

11. The apparatus of claim 10, wherein said adapter is configured for detachment from said contacts and when detached may be rotated between at least two predetermined positions and reconnected to said contacts to permit selection of the polarity of electrical power transmitted from said supply conduit to said light source.

12. The apparatus of claim 11, wherein said two predetermined positions are disposed at 180 degrees relative to each other.

13. The apparatus of claim 9, wherein one end of a lead of said adapter comprises a slide contact.

14. The apparatus of claim 10, wherein said leads and contacts are connected by non-rotatable plug contacts.

15. The apparatus of claim 9, further comprising a light conductor positioned to conduct light from said light source to a selected treatment site.

16. The apparatus of claim 9, wherein the adapter is selectively switchable by rotation.

17. The apparatus of claim 9, wherein the apparatus comprises a sleeve defining a hollow interior space and an end cap sized to fit an end of a sleeve, and wherein the adapter is configured to be received in the sleeve with the end cap fitted to the sleeve to secure the adapter in place.

18. A handpiece system comprising
a supply hose having a distal end coupling device with axially offset supply contacts for supplying electrical power transmission from an external power source,
a handle sleeve having a light source contained therein with receiving contacts for connecting the light source to receive electrical power from said coupling device, and
an adapter having an adapter body connectible between said coupling device and light source and having first and second electrical leads connectible to the power source, wherein the adapter body has a first body end, a second body end, and a substantially straight longitudinal axis extending between the first and second body ends, wherein the first body end is adapted for attachment to one of the coupling device and the light source and the second body end is adapted for attachment to the other of the coupling device and the light source, wherein the adapter is selectively switchable without disassembly by a manual operation to move the electrical leads of the adapter relative to the supply contacts of the supply conduit to match the polarity of electrical power transmitted from the power source to that needed by the light source, and wherein the first adapter electrical lead comprises a first end and the second adapter electrical lead comprises a second end, said first and second ends being axially offset along the longitudinal axis of the adapter body such that the first end is located a first distance from the first body end and the second end is located a second distance from the first body end where the first distance is not equal to the second distance, and wherein the adapter comprises a hollow space for releasable accommodation of a coupling spigot, and wherein said first and second ends are located at the periphery of said hollow space.

19. The handpiece system of claim 18, wherein the electrical leads of the adapter comprise first and second electrical power transmission leads and said receiving contacts comprise first and second contacts to which said leads may be detachably connected in a first orientation with said first lead connected to said first contact and said second lead connected to said second contact, and said adapter is configured for rotation about an axis thereof to a second orientation whereby said first lead is connected to said second contact and said second lead is connected to said first contact to reverse the polarity of electrical power transmitted to the operating element.

20. The handpiece system of claim 18, wherein said adapter is configured for detachment from said receiving contacts and when detached may be rotated between at least two predetermined positions and reconnected to said receiving contacts to permit selection of the polarity of electrical power transmitted from said supply hose to said light source.

21. The handpiece system of claim 18, wherein the adapter is selectively switchable by rotation.

22. An adapter for use in a handpiece system that includes a supply conduit and a medical instrument having an electrical operating element thereon, the adapter comprising:
an adapter body and first and second adapter electrical leads with respective first and second axially offset slide contacts, wherein the first and second adapter electrical leads are connectible to a voltage or power source, and wherein said adapter body has a first body end, a second body end, and a substantially straight longitudinal axis extending between the first and second body ends, wherein the first body end is adapted for attachment to one of the supply conduit and the medical instrument and the second body end is adapted for attachment to the other of the supply conduit and the medical instrument;

wherein, when the adapter is in place between the supply conduit and the medical instrument and the slide contacts are connected, electrical power is received by the adapter from the supply conduit and transmitted through the adapter to the operating element, and wherein the adapter is selectively switchable without disassembly by a manual operation to move the adapter electrical leads relative to the supply conduit to match a polarity of the electrical power transmitted from the supply conduit to a polarity required by the operating element, wherein the adapter comprises a hollow space for releasable accommodation of a coupling spigot, and wherein said first and second axially offset slide contacts are located at the periphery of said hollow space.

23. The adapter of claim 22, wherein the hollow space is configured to accommodate a rotary coupling of the supply conduit comprising the coupling spigot, wherein each of the first and second adapter electrical leads comprises a first portion which is disposed circumferentially around the hollow space, so that the rotary coupling may be accommodated between these first portions of the leads, and wherein the first adapter electrical lead comprises a first end that provides the first slide contact and the second adapter electrical lead comprises a second end that provides the second slide contact, said first end and second end extending towards the hollow space.

24. A light emitting apparatus comprising:
a light source requiring a selected polarity of power supply connected to a supply conduit through which electrical power is transmitted; and
an adapter connected between the light source and the supply conduit, said adapter having a first body end, a second body end, a substantially straight longitudinal axis extending between the first and second body ends, wherein the first body end is adapted for attachment to one of the supply conduit and the light source and the second body end is adapted for attachment to the other of the supply conduit and the light source, the adapter comprising first and second adapter electrical leads and respective first and second axially offset slide contacts, wherein the first and second adapter electrical leads are connectible to a voltage or power source, said adapter being selectively switchable without disassembly by a manual operation to move the adapter electrical leads relative to the supply conduit to match the polarity of electrical power transmitted from the supply conduit to that required by the light source, wherein the first adapter electrical lead comprises a first end and the second adapter electrical lead comprises a second end, said first and second ends being axially offset along a the longitudinal axis of the adapter such that the first end is located a first distance from the first body end and the second end is located a second distance from the first body end, where the first distance is not equal to the second distance, wherein the adapter comprises a hollow space for releasable accommodation of a coupling spigot, and wherein said first and second ends are located at the periphery of said hollow space.

25. The light emitting apparatus of claim 24, wherein the hollow space is configured to accommodate a rotary coupling of the supply conduit comprising the coupling spigot, wherein each of the first and second adapter electrical leads comprises a first portion which is disposed circumferentially around the hollow space, so that the rotary coupling may be accommodated between these first portions of the leads, and wherein the first end of the first adapter electrical lead provides the first slide contact and the second end of the second adapter electrical lead provides the second slide contact, said first end and second end extending towards the hollow space.

26. A handpiece system comprising
a supply hose having a distal end coupling device with supply contacts comprising axially offset slip rings for supplying electrical power transmission from an external power source,
a handle sleeve having a light source contained therein with receiving contacts for connecting the light source to receive electrical power from said coupling device, and
an adapter connectible between said coupling device and light source, said adapter having a first body end, a second body end, and a substantially straight longitudinal axis extending between the first and second body ends, wherein the first body end is adapted for attachment to one of the supply hose and the light source and the second body end is adapted for attachment to the other of the supply hose and the light source, the adapter comprising first and second adapter electrical leads and respective first and second axially offset slide contacts connectible to the supply contacts, wherein the first and second adapter electrical leads are connectible to the external power source, wherein the adapter is selectively switchable without disassembly by a manual operation to move the transmission leads relative to the supply hose to match the polarity of electrical power transmitted from the power source to that needed by the light source, wherein the adapter comprises a hollow space for releasable accommodation of a coupling spigot, and wherein said first and second axially offset slide contacts are located at the periphery of said hollow space.

27. The handpiece system of claim 26, wherein the supply conduit comprises a rotary coupling which comprises the axially offset slip rings and the coupling spigot and wherein the hollow space is configured to accommodate the rotary coupling of the supply conduit, wherein each of the first and second adapter electrical leads comprises a first portion which is disposed circumferentially around the hollow space, so that the rotary coupling may be accommodated between these first portions of the leads, and wherein the first adapter electrical lead comprises a first end that provides the first slide contact and the second adapter electrical lead comprises a second end that provides the second slide contact, said first end and second end extending towards the hollow space.

* * * * *

UNITED STATES PATENT AND TRADEMARK OFFICE
CERTIFICATE OF CORRECTION

PATENT NO. : 7,534,104 B2  Page 1 of 1
APPLICATION NO. : 10/781030
DATED : May 19, 2009
INVENTOR(S) : Rainer Schneider It is certified that error appears in the above-identified patent and that said Letters Patent is hereby corrected as shown below:

Column 3, line 31, "handpiece system I" should read --handpiece system 1--.

Column 9, line 57, "offset along a the" should read --offset along the--.

Signed and Sealed this

Sixteenth Day of March, 2010

David J. Kappos
*Director of the United States Patent and Trademark Office*